US00PP10181P

United States Patent [19]

Wain

[11] Patent Number: Plant 10,181

[45] Date of Patent: Jan. 6, 1998

[54] CHRYSANTHEMUM PLANT NAMED 'ORIOLE'

[75] Inventor: Peter Wain, Portsmouth, United Kingdom

[73] Assignee: Cleangro Limited, Chichester, United Kingdom

[21] Appl. No.: 733,725

[22] Filed: Oct. 18, 1996

[51] Int. Cl.[6] ..... A01H 5/00

[52] U.S. Cl. ..... Plt./82.3

[58] Field of Search ..... Plt./74.1, 82.2, Plt./82.3

[56] References Cited

U.S. PATENT DOCUMENTS

P.P. 9,384 11/1995 Fuess ..... Plt./82.3

*Primary Examiner*—Howard J. Locker

*Attorney, Agent, or Firm*—C. A. Whealy

[57] ABSTRACT

A distinct cultivar of Chrysanthemum plant named 'Oriole' characterized by its vigorous and mounded growth habit; daisy-type inflorescences; orange ray florets and bright yellow disc florets; numerous inflorescences per plant; and good garden performance.

2 Drawing Sheets

The present invention relates to a new and distinct cultivar of Chrysanthemum plant, botanically known as *Dendranthema grandiflora* and referred to by the cultivar name Oriole.

The new cultivar is a product of a planned breeding program conducted by the inventor in Chichester, West Sussex, United Kingdom. The objective of the breeding program was to create new Chrysanthemum cultivars having desirable inflorescence colors and good garden performance.

The new cultivar originated from a cross made by the inventor of the Chrysanthemum proprietary selection P173/91 as the female, or seed, parent with the cultivar 'Empire Ventura' (U.S. Plant Pat. No. 9,384) as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Oriole'. These characteristics in combination distinguish 'Oriole' as a new and distinct cultivar:

1. Vigorous and mounded growth habit.
2. Daisy-type inflorescences.
3. Orange ray florets and bright yellow disc florets.
4. Numerous inflorescences per plant.
5. Good garden performance.

The cultivar Oriole has not been observed under all possible environmental conditions. The phenotype may vary somewhat with variations in environment such as temperatures, daylength and light intensity, without, however, any variance in genotype.

In side-by-side comparisons in Chichester, West Sussex, United Kingdom, under commercial practice, plants of the new Chrysanthemum have a more mounded habit, larger inflorescences and flower later than plants of the female parent, the proprietary Chrysanthemum selection P173/91 and the male parent, the Chrysanthemum cultivar 'Empire Ventura'. In addition, ray floret color of plants of the new Chrysanthemum is orange whereas ray floret color of plants of the cultivar 'Empire Ventura' are more yellow.

Plants of the new Chrysanthemum can be compared to the cultivar 'Grace' (U.S. Plant Pat. No. 7,642). However, in side-by-side comparisons conducted in Oxnard, Calif., under commercial practice, plants of the new Chrysanthemum differed from plants of the cultivar 'Grace' in the following characteristics:

1. Plants of the new Chrysanthemum are taller than plants of the cultivar 'Grace'.
2. Plants of the new Chrysanthemum have a more uniform plant habit than plants of the cultivar 'Grace'.
3. Plants of the new Chrysanthemum flower later than plants of the cultivar 'Grace'.
4. Inflorescences of the new Chrysanthemum have a tidy, uniform edge whereas inflorescences of the cultivar 'Grace' have a ragged, nonuniform edge.
5. Ray florets of the cultivar 'Grace' have a yellow-gold band at their base whereas ray florets of the new Chrysanthemum are solid orange and lack this band.
6. Plants of the new Chrysanthemum have longer peduncles than plants of the cultivar 'Grace'.
7. Inflorescences of plants of the cultivar Grace produce considerably more pollen than inflorescences of the new Chrysanthemum.

A detailed comparison of plants of the new Chrysanthemum and the cultivar Grace appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical flowering 16.5-cm container of 'Oriole' with one cutting in the container.

The second photograph comprises a close-up view of four leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar 'Oriole'

Commercial classification: Garden Chrysanthemum.

Parentage:

*Female, or seed, parent.*—*Dendranthema grandiflora* propietary selection P173/91.

*Male, or pollen, parent.*—*Dendranthema grandiflora* cultivar 'Empire Ventura' (U.S. Plant Pat. No. 9,384).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Vigorous and rapid growth rate. Mounded, uniform habit and freely branching.

*Plant height.*—About 20 cm.

*Lateral branch length.*—About 16 cm.

*Quantity of lateral branches after removal of apical meristem.*—3 to 4.

*Stem color.*—147C.

*Foliage description.*—Number of leaves per plant: About 48. Number of leaves per lateral branch: About 12. Leaf arrangement: Alternate. Leaf size, fully expanded. Length: About 4.5 cm. Width: About 4 cm. Leaf apex: Rounded, slightly apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.4 cm. Color: Young foliage adaxial surface: 147A. Young foliage abaxial surface: 147B. Fully expanded foliage adaxial surface: 147A. Fully expanded foliage abaxial surface: 147B. Venation adaxial surface: 147C. Venation abaxial surface: 147B. Petiole: 147C.

Flowering description:

*Appearance.*—Daisy inflorescence form. Inflorescences borne on terminals above foliage, arising from leaf axils. Disc and ray florets arranged acropetally on flat capitulum. Inflorescence is comprised of two whorls of short, wide ray florets, and a large disc. Uniform inflorescence edge.

*Flowering response.*—Under natural conditions, plants flower in the autumn. At other times of the year, inflorescence initiation and development can be induced under short day/long night conditions (at least 13.5 hours of darkness). Plants exposed to about 4 weeks of long day/short night conditions after sticking followed by photoinductive short day/long night conditions, flower about 49 days later.

*Quantity of inflorescences.*—About 6 to 8 inflorescences per flowering stem.

*Inflorescence size.*—Diameter: About 4 cm. Depth (height): About 1.3 cm. Diameter of disc: About 1.5 cm.

*Opening inflorescences.*—Bud shape: Slightly flattened. Bud size: Length: About 8 mm. Width: About 1 cm. Bud color: 169B.

*Ray florets.*—Shape: Spatulate. Size: Length: About 1.7 cm. Width: About 7.5 mm. Apex: Blunt, very slightly tri-dentate. Base: Acute. Margin: Entire. Texture: Velvety, smooth and glabrous. Aspect: Flat. Number of ray florets per inflorescence: About 30. Color: When opening adaxial surface: 25A. When opening abaxial surface: 21B. Mature, adaxial surface: 25A. Mature, abaxial surface: 21B. Fading to: 21A.

*Disc florets.*—Shape: Tubular. Size: Length: About 5 mm. Width: About 1 mm. Number of disc florets per inflorescence: About 160. Color: Immature: 154C. Mature: 1C.

*Peduncle.*—Aspect: Strong and angled about 25° to 35° to the stem. Length: First peduncle: About 4.5 cm. Fourth peduncle: About 6 cm. Texture: Pubescent. Color: 147C.

*Reproductive organs.*—Androecium: Present on disc florets only. Anther color: 14A. Pollen: Moderate, 14A in color. Gynoecium: Present on both ray and disc florets. Style color: 154C.

Disease resistance: No known Chrysanthemum diseases observed to date on plants grown under commercial greenhouse conditions.

Seed production: Seed production has not been observed.

CHART A

| CHARACTERISTIC | 'ORIOLE' | 'GRACE' |
|---|---|---|
| PLANT SHAPE | Mounded habit | Upright |
| PETIOLE LENGTH | About 2.4 cm | About 1.35 cm |
| INFLORESCENCE DIAMETER | About 4 cm | About 4.5 cm |
| INFLORESCENCE DEPTH | About 1.3 cm | About 9 mm |
| BUD SHAPE | Slightly flattened | Spherical |
| BUD COLOR | 169B | 163A |
| RAY FLORET SHAPE | Short and wide, spatulate | Narrow, strap-like |
| RAY FLORET APEX | Blunt, very slightly tri-dentate | Unevenly dentate ragged appearance |
| RAY FLORET LENGTH | About 1.7 cm | Variable, 1.7 to 2.4 cm |
| RAY FLORET WIDTH | About 7.5 mm | About 4.5 mm |
| RAY FLORET COLOR WHEN OPENING, ADAXIAL | 25A | 24A |
| RAY FLORET COLOR, WHEN OPENING, ABAXIAL | 21B | 17B |
| RAY FLORET COLOR, MATURE, ADAXIAL | 25A | 23A |
| RAY FLORET COLOR, MATURE, ABAXIAL | 21B | 17C |
| RAY FLORET COLOR FADING TO | 21A | 23B |
| NUMBER OF DISC FLORETS PER INFLORESCENCE | About 160 | About 138 |
| DISC FLORET COLOR, IMMATURE | 154C | 154D |
| DISC FLORET COLOR, MATURE | 1C | 154C |
| DIAMETER OF DISC | About 1.5 cm | About 1.1 cm |
| PEDUNCLE LENGTH, FIRST | About 4.5 cm | About 4 cm |
| PEDUNCLE LENGTH, FOURTH | About 6 cm | About 5.7 cm |
| AMOUNT OF POLLEN | Moderate | Abundant |

It is claimed:

1. A new and distinct cultivar of Chrysanthemum plant named 'Oriole', as illustrated and described.

* * * * *

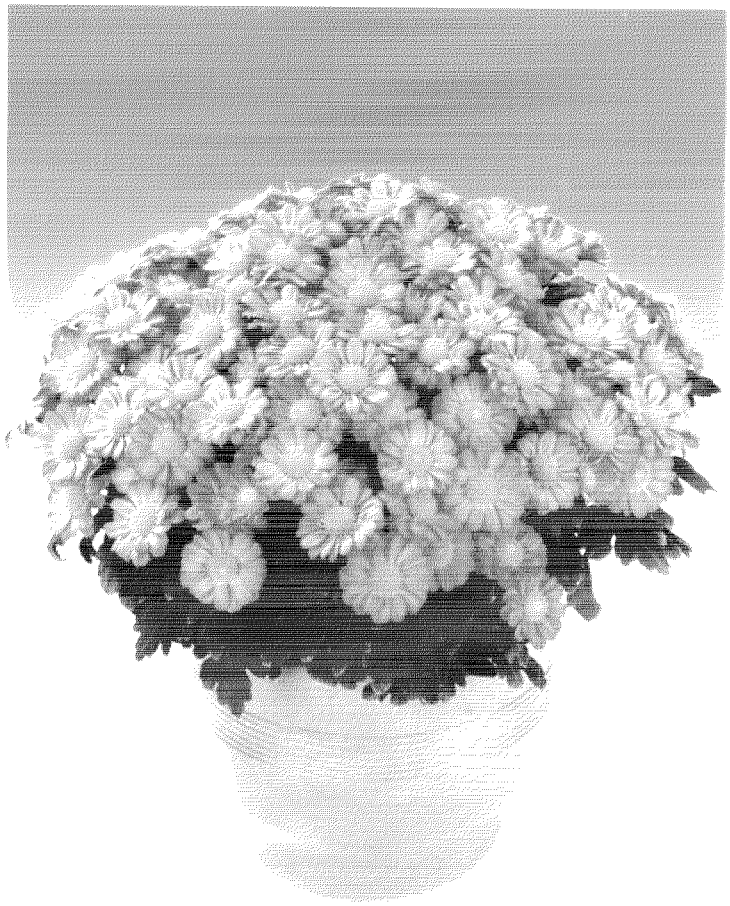

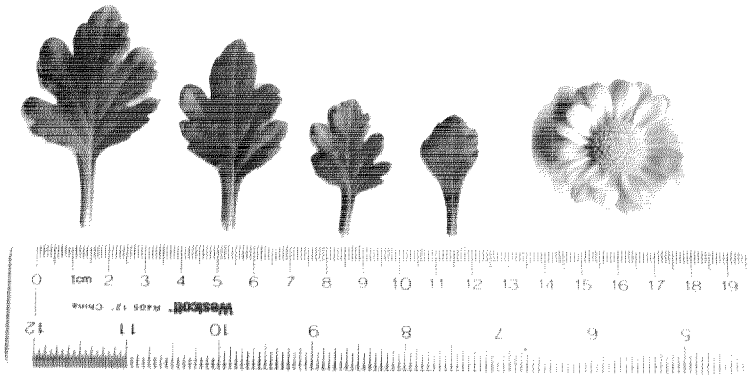
5 6 7 8 9 10 11 12
Westcott R405 12" China
0 1cm 2 3 4 5 6 7 8 9 10 11 12 13 14 15 16 17 18 19